United States Patent
Kurtz

[19]

[11] Patent Number: 6,058,160

[45] Date of Patent: May 2, 2000

[54] PHOTO-SENSOR FIBER-OPTIC STRESS ANALYSIS SYSTEM

[75] Inventor: David S. Kurtz, State College, Pa.

[73] Assignee: Hypernex, Inc., State College, Pa.

[21] Appl. No.: 09/144,932

[22] Filed: Sep. 1, 1998

Related U.S. Application Data

[62] Division of application No. 08/823,971, Mar. 25, 1997, Pat. No. 5,828,724.

[51] Int. Cl.[7] .................................................. G01N 23/04
[52] U.S. Cl. .............................. 378/70; 378/72; 378/87
[58] Field of Search .............................. 378/70, 72, 98.2, 378/98.8, 86, 87

[56] References Cited

U.S. PATENT DOCUMENTS

| | | |
|---|---|---|
| 4,489,425 | 12/1984 | Borgonovi . |
| 4,686,631 | 8/1987 | Ruud . |
| 5,125,016 | 6/1992 | Korhonen et al. . |
| 5,148,458 | 9/1992 | Ruud . |
| 5,414,747 | 5/1995 | Ruud et al. . |
| 5,629,524 | 5/1997 | Stettner et al. . |
| 5,724,401 | 3/1998 | Kurtz et al. . |
| 5,848,122 | 12/1998 | Kurtz ........................................ 378/80 |

OTHER PUBLICATIONS

Noyan, I.C. and Cohen, J.B., "Residual Stress," Springer–Verlag, ISBN 0–387–96378–2, (1987), pp. 4–7, 74–110, and 116–125.

Noyan, I.C. and Goldsmith, C.c., "Thermal Stress Relaxation in Vapor Deposited Thin Films," Advances in X–ray Analysis, 34, 587, (1991).

Crowder, C.E. et al., "The Measurement of Triaxial Residual Stress in Polymer–Coated Aluminum Circuitry in Microchip Modules," Advances in X–ray Analysis, 36, 231, (1993).

Tencor FLX, "Thin Film Stress Measurement Systems," (1994).

*Primary Examiner*—David V. Bruce
*Assistant Examiner*—Michael J. Schwartz
*Attorney, Agent, or Firm*—Steven J. Hultquist; William A. Barrett; Edward H. Green, III

[57] ABSTRACT

An x-ray diffraction system for determining stress in integrated circuit materials includes a source of x-rays (3) that are directed toward a sample holding mechanism for diffracting from the test sample (8). An x-ray detector (14) is arranged for detecting high back reflected diffracted x-ray intensity data representing stress in the test sample. A two-dimensional detection and storage arrangement (24) is arranged for detecting and storing the data representing stress in the test sample. A data processor (2) accesses the stored data from the two-dimensional detection and storage arrangement and processes the data representing stress in the test sample to determine stress in the test sample.

20 Claims, 6 Drawing Sheets

PHOTO-SENSOR FIBER-OPTIC STRESS ANALYSIS SYSTEM

This a Divisional of Ser. No. 08/823,971 filed Mar. 25, 1997 now U.S. Pat. No. 5,828,724.

BACKGROUND OF THE INVENTION

1. Field of the Invention

The present invention relates to an apparatus and a method for x-ray diffraction analysis of materials, e.g., semiconductor materials or other crystalline materials, using a photo-sensor fiber-optic stress analysis system.

2. Description of the Related Art

X-ray diffraction is a well known technique for measuring stress in solid materials. X-rays diffracted from the surface of a material provide direct information about the spacing between particular atomic planes of the material. X-rays impinging on a set of atomic planes will scatter in all directions. Constructive interference of the scattering x-rays occurs only at particular angles that the scattering x-rays make with the particular atomic planes, and is dependent on the spacing of the particular atomic planes. This atomic spacing information is represented in the form of diffracted x-ray intensity versus the diffraction angle from the particular atomic planes of the material, and is governed by the Bragg Equation expressed as:

$$\lambda = 2d \sin\theta$$

where $\lambda$ = wavelength of the diffracted radiation d = atomic lattice spacing of a particular set of atomic planes $\theta$ = Bragg angle.

Constructive interference of scattered x-rays occurs when the incident angle of the x-ray beam with the particular set of atomic planes is equal to the diffracted angle, that angle $\theta$ (referred to as the Bragg angle) satisfying the Bragg Equation. Constructive interference results in intensity maxima, also referred to as diffraction peaks. Each particular set of atomic planes of a material will have an associated diffraction peak which occurs at a particular $\theta$ angle which satisfies the Bragg Equation. It is common to refer to the $2\theta$ angle where the factor of two accounts for both the incident x-ray beam angle with the particular atomic planes, and the diffracted beam angle with the same atomic planes. When a region of material exhibits residual stress, or is under applied stress, the spacing of the atomic planes can increase or decrease with respect to the spacing of the atomic planes in the unstressed state. Thus according to the Bragg Equation when a material is stressed the diffraction peaks will shift to a slightly different Bragg angle, i.e., the $\theta$ value changes slightly due to a change in spacing of the atomic planes. X-ray diffraction can be used to directly determine the angular shift of the diffraction peak. The change in atomic spacing can be used to determine the strain of the region of material being examined. Stress is subsequently calculated from the strain using the elastic constants of the material.

The preferred atomic planes for x-ray diffraction stress analysis are those which occur at higher diffraction angles, or correspondingly at lower atomic spacing. The x-ray diffraction peaks (or atomic planes) at these higher angles are generally of low intensity compared to diffraction peaks occurring at lower diffraction angles, but they exhibit a larger position shift because of changes in stress than the low angle peaks. Thus the high angle peaks provide a greater degree of accuracy in determining strain and stress. The preferred high angle diffraction peaks for stress analysis are also referred to as high backreflected peaks and generally occur at a $2\theta$ angle of greater than 100°, and preferably in the range of 130° to 165°.

Instruments used to measure stress by x-ray diffraction typically employ a monochromatic x-ray source and either a mechanical scanning point detector or one or more position sensitive detectors. These systems all determine the diffraction peak locations, and the change in the peak location due to stress. The x-ray source, the material being examined, and the detector(s) are arranged in controlled angular relationships in order to measure stress. A thorough description of stress analysis by x-ray diffraction can be found in a book titled ìResidual Stress, Measurement by Diffraction and Interpretationî, authored by I. C. Noyan and J. B. Cohen (Published by Springer-Verlag 1987, ISBN 0-387-96378-2).

Fiber-optic based position sensitive detectors used for stress analysis are described in U.S. Pat. Nos. 4,686,631; 5,148,458; and 5,414,747, issued to Ruud et al.; in U.S. Pat. No. 4,489,425, issued to Borgonovi; and in U.S. Pat. No. 5,125,016, issued to Korhonen.

U.S. Pat. No. 4,686,631 discloses and claims a method for obtaining calibration coefficients for residual internal stress measurements in polycrystalline specimens without the requirement of accurately controlling or auxiliarily measuring specimen-to-detector distance in an x-ray diffraction system for stress analysis. The patent discloses single exposure technique (SET) and multiple exposure technique (MET) internal stress measurement methods as well as methodology for verification of coefficient validity. The disclosed technique for obtaining calibration coefficients for stress analysis is described with reference to the use of a multi-channel x-ray detector, which may be a position sensitive detector, a position sensitive proportional detector, or a position sensitive scintillation detector.

In the position sensitive scintillation detector, as disclosed in U.S. Pat. No. 4,686,631, thin scintillation coatings placed on the input face of fiber-optic channel bundles convert diffracted x-rays into visible light and transmit the visible light into the fiber-optic bundles. The fiber-optic bundles then transmit the visible light, derived from diffracted x-ray radiation, to separate photodiode arrays (PDAs). The photodiode arrays are a part of a scanner subassembly typified by an individual linear photodiode array including 512 pixels arranged in a single continuous row of 512 pixels long and one pixel wide. Each fiber-optic bundle transmits light to a separate linear diode array. The linear diodes are arranged in proximity such that they fit within the active area of a circular image intensifier. The individual diodes and associated precharged capacitors are arranged in a face-to-face relationship to the intensified image being received from the corresponding fiber-optic bundles. The photodiodes are responsive to visible light for storing in the capacitors an electronic signal determined to have a functional relationship to the visible light impinging upon the photodiodes. The output of each diode array represents the intensity of the diffracted x-ray beam as a function of the diffraction angle, thus showing the diffraction peak location and shape (referred to herein as a one dimensional diffraction spectrum) from each fiber-optic bundle. The diffraction peak location provided by each of the fiber-optic bundles when analyzed together with data from unstressed material enables determination of the stress in the material.

U.S. Pat. No. 5,148,458 discloses a system for simultaneous measurement of phase composition and residual stress, utilizing an x-ray detector which may be of the type disclosed and claimed in U.S. Pat. No. 4,686,631. There are three position-sensitive x-ray detectors fixedly mounted along a circular arc, an x-ray source for impingement of a beam of x-rays on the center of the circle represented by the arc, and distribution spectra analysis apparatus. A method described includes directing a beam of x-rays on a polycrystalline sample and receiving and detecting resultant Bragg diffraction x-rays by three stationary position-sensitive x-ray detectors located along a circular arc. The sample is located at the center of the circle of the arc. Diffracted x-rays received by two of the detectors are analyzed to determine residual stress, and diffracted x-rays received by the third detector are analyzed to determine phase composition of the sample.

Both U.S. Pat. Nos. 4,686,631 and 5,148,458, describe a linear photodiode array as a position-sensitive detector in their systems. Photodiode arrays, however, have a significant shortcoming as photo-sensor array detectors for fiber-optic stress analysis systems. The photodiode arrays have a large electronic charge storage capacity but that is accompanied by undesirably high background noise levels (dark current and read noise). This makes them optimal for measuring higher light intensities, such light intensity being much greater than the background noise created in the diodes. The diffracted x-ray peaks of many materials and structures used in stress analysis are often very weak, i.e., the peak-to-background signal ratio is low, and the overall diffracted x-ray intensity is much lower than the incident x-ray beam intensity. The scintillation process might typically be only 10% efficient, thus the resultant intensity of the light image entering the fiber-optic bundles is extremely weak, and the intensity of the light peak representing the corresponding x-ray diffraction peak is only slightly greater than the background light intensity on either side of the light peak. To compensate for the extremely weak incoming light signal, an image intensifier is required for PDAs, however, the intensifier magnifies the background light on either side of the diffraction light peak as well. When the high internal noise levels of the PDAs are added to the incoming intensified light signal, the total background light in the final output spectrum will further reduce the peak-to-background signal ratio. Very long data acquisition times are often required for such weak diffraction peaks, and in some cases the peaks are never observed regardless of the acquisition time. The PDAs are also limited in available sizes and in the total amount of PDA active area that can be mated with a single image intensifier.

U.S. Pat. No. 5,125,016 discloses a procedure and two apparatus variations for measuring stress based on x-ray diffraction. One apparatus includes two fiber-optic light cables, each covered with a thin scintillation coating and connected to image intensified silicon diode arrays. The thin scintillation coatings placed on the input face of fiber-optic light cables convert diffracted x-rays into visible light and transmit the visible light first through an image intensifier, then on to a series of silicon photo-diodes. The data from the silicon photo-diodes fed to an analog to digital converter, then to a multichannel analyzer and a computer for graphical display. The fiber-optic light cables are rectangular with, e.g., a cross-section of 1 millimeter by 2 millimeters. In the second apparatus, a linear series of photo-diodes coated with a fluorescent film are employed as the detector, without fiber-optic light cables interposed between the fluorescent film and the diode array.

U.S. Pat. No. 5,414,747 discloses a system for real-time analysis of a plated specimen, to determine analytically variables such as: composition of the substrate and plating; plating thickness; plating depth (under an overlayer); analysis of crystal phase depth concurrently with phase composition; preferred crystalline orientation; substrate strain; crystallinity; and grain size. The apparatus includes a plurality of position-sensitive detector surfaces, an x-ray source for impinging x-rays on a plated specimen, and plural detector surfaces positioned on either side of the incident x-ray beam from the x-ray source, so that the detector surfaces detect x-rays diffracted from a plurality of crystallographic planes of the plated specimen at various angles. The first and second detector surfaces are positioned at different distances from the specimen, and means are provided for analyzing the spectra of diffracted peaks of x-radiation diffracted from the plural crystallographic planes of the plated specimen.

U.S. Pat. No. 5,414,747 also discloses that two fiber-optic detectors may be coupled by an optical amplifier to silicon diode arrays. The diode arrays convert the amplified coherent optical signals into electrical signals which are then transmitted to a central processor or computer for spectra analysis. The patent notes that other types of position-sensitive detectors may be employed, such as charge-coupled devices (CCD) or other one-dimensional or two-dimensional x-ray sensitive devices. There is no description of how to arrange and operate the system with a CCD device to produce a readable signal. Numerous changes must be made for such a system to be operable, and to further operate it in an optimized fashion. Direct replacement of a PDA by a CCD does not appear to be possible.

Most commercial CCDs will not be optimal, nor even adequate for replacing the diode arrays of the x-ray diffraction system taught by U.S. Pat. No. 5,414,747. It is not at all clear from the disclosure of U.S. Pat. No. 5,414,747 which CCDs will work or not and how those that might work should be arranged for operation. Most commercial CCDs are lens-coupled, with fixed shutter speeds and unreasonably high noise levels for low light scientific applications. Newer scientific slow scan image intensified CCDs offer extremely high sensitivity, and controllable shutter speeds, but almost all image intensified CCDs are isolated by a lens coupling and are evacuated for low temperature operation in order to reduce the noise. Lens coupled CCDs cannot be directly coupled to fiber-optic bundles. Scientific slow scan CCDs that are not image intensified are often fiber-optically coupled, but they do not offer the high level of sensitivity preferred for x-ray diffraction stress analysis that image intensified CCDs offer.

PDAs used for stress analysis are one dimensional arrays as disclosed in U.S. Pat. Nos. 4,686,631, 5,148,458, 5,414,747, and 5,125,016. The unmodified graphical output from PDAs represents a one dimensional diffraction spectrum (intensity versus diffraction angle) showing the diffraction peak location, intensity and shape. The diffraction peak is shown on a graphical plot of diffracted intensity in the vertical direction, or y scale, versus the diffraction angle in the horizontal direction, or x scale. A stress in the material being examined will give rise to a shift in the diffraction angle (or position) of the diffracted x-ray peak from its unstressed position. To accurately determine a very small position shift in the diffraction peak, a mathematical curve fitting procedure is typically used to precisely determine the exact angular location of the peak. Desirable CCDs for stress analysis are two dimensional arrays and do not output data for a one dimensional diffraction spectrum, rather they output data for a two dimensional image which cannot be processed by the teachings of U.S. Pat. Nos. 4,686,631, 5,148,458, 5,414,747, and 5,125,016.

U.S. Pat. No. 4,489,425 describes an x-ray diffraction apparatus for making stress measurements using a single position sensitive area detector which can capture x-rays over a large planar region. The apparatus discloses a single rigid fiber-optic tapered array with a large two dimensional planar input area coated with a scintillating material. X-rays are diffracted from the sample surface onto a large planar face input area of the detector and are converted to a visible light image which is then transported to the CCD. The smaller output end of the fiber-optic taper is coupled to a two dimensional CCD and produces a two dimensional image representing a planar intersection of the full x-ray diffraction cone, or a major portion thereof, for subsequent stress analysis. The image consists of an ellipse, or major portion thereof, the total shape of which is analyzed to provide stress information. The large planar face input area of the detector makes it difficult to achieve and control the desired series of angular relationships between the detector, x-ray source and material being examined.

It would therefore be a significant advance in the art, and is an object of the present invention, to provide for the x-ray diffraction analysis of materials, an improved x-ray detector system which overcomes deficiencies of the prior art.

SUMMARY OF THE INVENTION

The aforementioned problems are resolved by an x-ray diffraction system for determining stress in integrated circuit materials. The system includes a source of x-rays that are directed toward a sample holding mechanism for diffracting from the sample. An x-ray detector is arranged for detecting high back reflected diffracted x-ray intensity data representing stress in the sample. A two-dimensional detection and storage arrangement is arranged for detecting and storing the data representing stress in the sample. A data processor accesses the stored data from the two-dimensional detection and storage arrangement and processes the data representing stress in the sample to determine stress in the sample.

A method using a two fiber-optic bundle detector arrangement includes a binning procedure-based algorithm.

BRIEF DESCRIPTION OF THE DRAWINGS

A more complete understanding of the invention may be derived by reading the following detailed description with reference to the drawings wherein.

DETAILED DESCRIPTION OF THE INVENTION, AND PREFERRED EMBODIMENTS THEREOF

An improved x-ray diffraction system for x-ray diffraction analysis of materials, e.g., semiconductor, conductor, or other materials used in integrated circuits and solid state devices, is to be described. The system can analyze stress in those materials as well as their composition, texture, dimensional characteristics, and other x-radiation diffraction-detectable characteristics.

The disclosures of the aforementioned Ruud patents are hereby incorporated herein by reference in their entirety by reference thereto.

Figure 1:
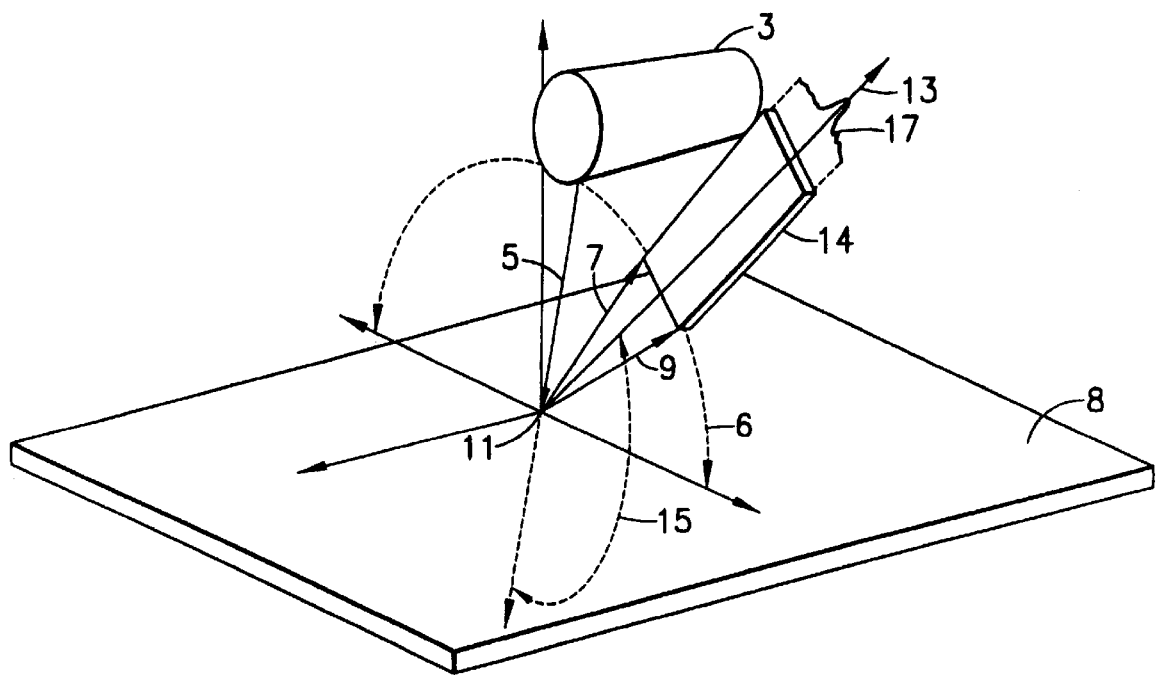
FIG. 1 is a general representation of the positional relationship between the x-ray source and one of the fiber-optic bundle detectors showing the angular relationship of the incident and diffracted x-ray beams with respect to the material surface.

FIG. 1 shows the geometrical relationship of an incident x-ray beam 5, emanating from an x-ray source 3, and one fiber-optic bundle detector 14. A second fiber-optic bundle detector should be mounted on the other side of the x-ray source, as further shown in FIG. 3, but is not shown in FIG. 1 for clarity purposes. The x-ray source 3 is a commercially available monochromatic source. The incident x-ray beam 5 diffracts off the surface of test sample material 8 at the measurement location 11. The fiber-optic bundle detector 14 is positioned such that its long cross-sectional dimension lies tangent to a focusing arc 6, or 2θ arc. The focusing arc also defines the 2θ angular direction. The uppermost diffraction angle impinging on detector 14 is defined by a vector 7, while the lower most diffraction angle impinging on detector 14 is defined by another vector 9. The diffraction peak angular location is defined by a third vector 13. The angular position of the diffraction peak is defined as a function of the incident x-ray beam vector 5 and the diffracted beam vector 13, (which runs through the center of the peak). This angle is referred to as the 2θ angle and is shown as arc 15 in FIG. 1. It is the angle between the extension of the incident x-ray beam vector 5, extended through the measurement location 11, and vector 13 identifying the diffraction peak location.

Figure 2:
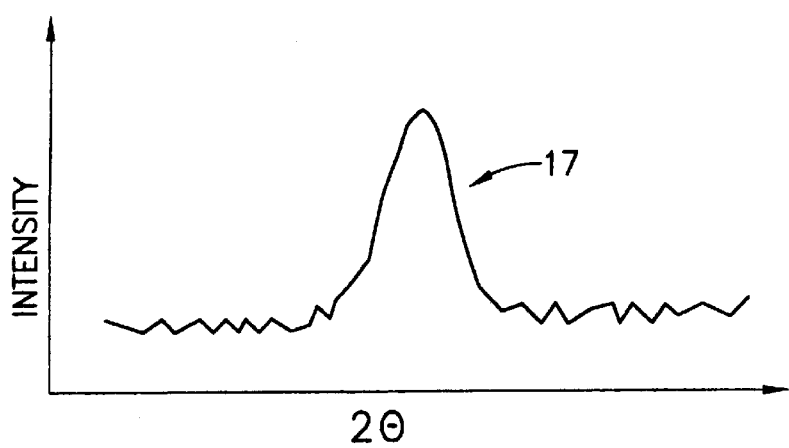
FIG. 2 is a one dimensional diffraction spectrum represented by diffraction intensity versus 2θ.

FIG. 2 shows a typical one dimensional diffraction spectrum output 17 required for stress analysis. The one dimensional diffraction spectrum 17 is a graph of x-ray intensity data representing stress in the test sample 8 and taken across the long cross-sectional dimension of fiber-optic bundle 14 of FIG. 1. It is a measure of the diffracted x-ray intensity along the 2θ arc where the fiber-optic detector is positioned. Crystallographic planes of the material give rise to intensity maxima, or diffraction peaks, occurring at particular 2θ angles governed by the Bragg Equation. The location of the diffraction peak on the 2θ arc in a stressed material, compared to the location of the same diffraction peak on the 2θ arc in an unstressed state, forms the basis for stress determination. To accurately describe the diffraction peak location it is highly desirable to fit a mathematical curve to the diffraction spectrum 17, since the peaks are typically of low intensity and quite broad. There are known methods in the art for doing this, but the line spectrum of FIG. 2 is first required for a curve fitting procedure to be applied.

Fiber-optic bundles for the individual detectors for sensing diffraction peaks on either side of the Debye ring, should be sized in cross-section to match the size of a 2-D photo-sensor array when grouped together and mated to the 2-D photo-sensor array.

Figure 3:
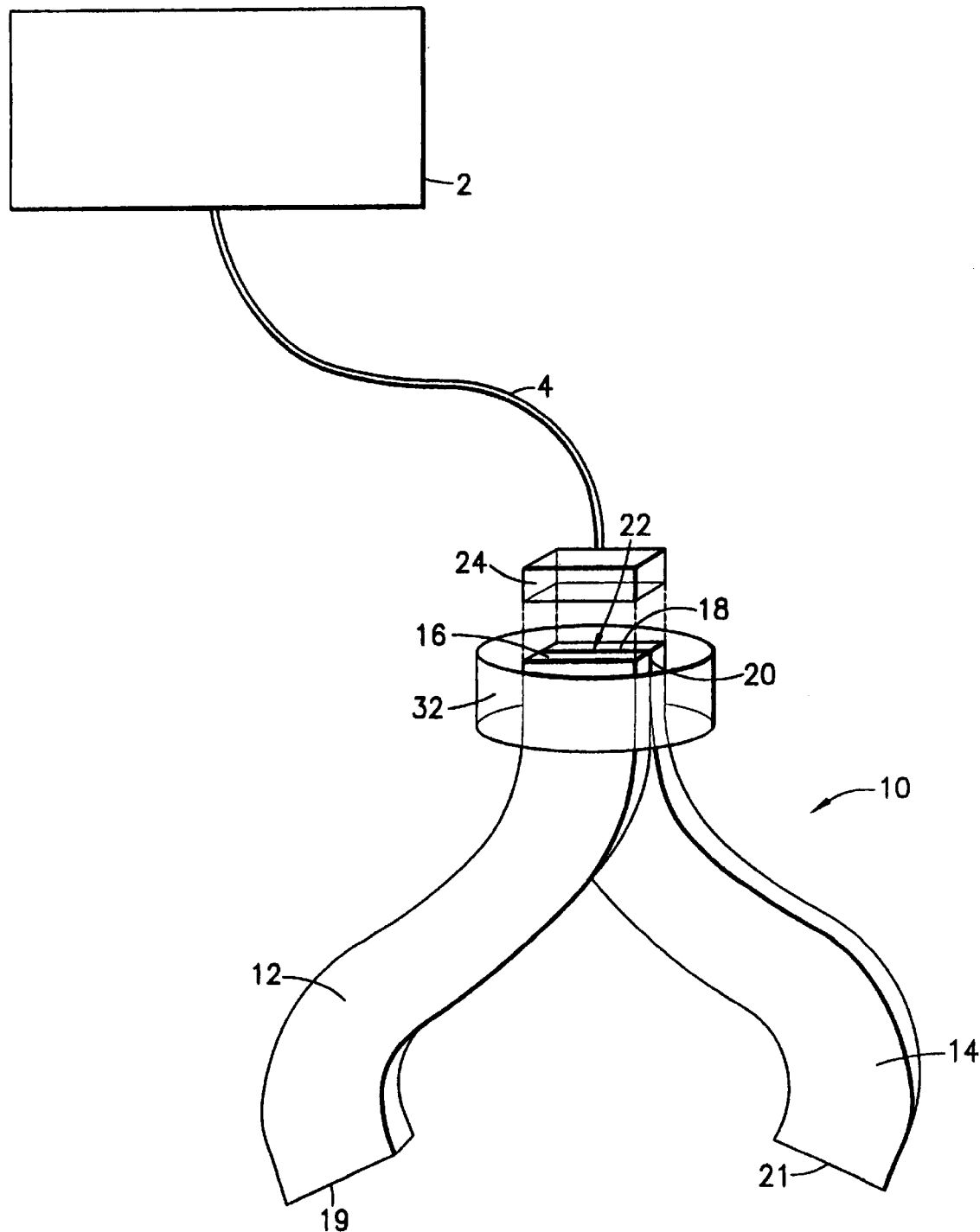
FIG. 3 is a perspective schematic view of a fiber-optic assembly comprising two fiber-optic bundles mated to a 2-D photo-sensor array, in which fiber-optic arrays form individual detectors for diffraction peaks on either side of the Debye ring and are sized to match the size of the 2-D photo-sensor array.

As shown in FIG. 3, the 2-D photo-sensor array 24 employed in the x-ray diffraction system of the present invention is combined with a minimum of two fiber-optic arrays to form the detector geometry. A fiber-optic bundle/2-D photo-sensor array 10 comprises two flexible fiber-optic bundles 12 and 14, which are suitably sheathed with a flexible protective light blocking material (not shown in FIG. 3). The flexible sheathing provides mechanical protection for the optical fibers and prevents any ambient light from entering the optic fibers. Such flexible sheathing extends over the length of the fiber-optic bundles 12 and 14 but does not extend over the end faces of the bundles. The only light that enters input ends 19 and 21 of the fiber-optic bundles should be the light generated by the x-ray diffraction process. Fiber-optic bundles 12 and 14 are mated at output ends 16 and 18 in the position shown, so that the output ends 16 and 18, respectively, are in longitudinal and width-wise register with one another. The fiber-optic bundles 12 and 14 should be sized in cross-section so that the combined cross-section matches the size of the 2-D photo-sensor array 24 when mated to the 2-D photo-sensor array. The output end portions of the respective fiber-optic bundles have a partially light-tight film 20 therebetween, and present a composite face 22 for coupling with a fiber-optic face plate of the single 2-D charge coupled device 24. The output ends 16 and 18 of the respective fiber-optic bundles thus are preferably planarized by any suitable planarization techniques, including polishing or otherwise abrading the ends, to render the same coplanar in relation to each other (when the end portions of the respective fiber-optic bundles are disposed in the fixture in their final assembled conformation).

The individual fiber-optic bundles 12 and 14 are arranged into a composite bundle at the output ends 16 and 18 using a particular rigid fixture. The output face of this composite bundle end is fabricated for direct optical coupling to the 2-D photo-sensor array 24, and also sized to match the shape of the active area of the 2-D photo-sensor array. The individual fiber-optic bundles 12 and 14 require robust light blocking sheathing, to prevent undesirable ambient light from entering each bundle, and to mechanically protect each bundle. This sheathing would normally prevent the fiber-optic bundles from being arranged into a closely spaced composite bundle at the output end. The rigid fixture of the present invention enables termination of such light blocking sheathing prior to the output ends 16 and 18, allowing the output ends to be brought together in a close packed arrangement, while still maintaining mechanical protection and light blocking.

The input end 19 of fiber-optic bundle 12, and input end 21 of fiber-optic bundle 14 may be suitably arranged in a non-contiguous fashion for receiving x-radiation diffracted from the test sample 8 of FIG. 1 on which x-radiation is impinged in the first instance. The region of each of the fiber-optic bundles 12 and 14 near the input faces 19 and 21 is fused solid while the central region of each of the bundles 12 and 14 is left flexible. X-radiation impinging on the input ends 19 and 21 of the fiber-optic bundles 12 and 14 is converted from x-radiation to visible light by a scintillation coating on the end surfaces of the respective fiber-optic bundles. Useful scintillation coatings include gadolinium oxy-sulfide doped with terbium or europium, yttrium oxy-sulfide doped with europium, lanthanum oxy-sulfide doped with europium, and zinc sulfide doped with cadmium. A very thin light tight film is placed over the scintillation coating to ensure that no ambient light enters the fiber-optic bundles through the scintillation coating (which is not adequately light tight itself). This light tight film is only thick enough for light blocking, and is preferably of low atomic mass material, to enable maximum x-ray penetration. Intensity of the visible light generated by the scintillation coating is proportional by position in the x-ray detector with the intensity of the incident x-rays. The fiber-optic bundles 12 and 14 provide a position-sensitive media for transmitting the intensity of the visible light image, in direct proportion to the incident x-ray intensity, to the CCD photo detector 24.

The output ends 16 and 18 of the respective fiber-optic bundles 12 and 14 assembly are encapsulated in a potting mass 32. The potting mass may be formed by curing of a suitable potting resin composition. For example, the potting composition may comprise a room temperature curable epoxy composition, a UV-curable acrylic resin composition, a polyester potting material, or any other suitable composition which is usefully employed to fix the registered end portions 16 and 18 of the mated fiber-optic bundles to one another. Such potting may be carried out with a potting fixture and by known techniques.

In this fiber-optic bundle/2-D photo-sensor array 10, the 2-D photo-sensor array 24 should be sized to allow for sufficient angular range of $2\theta$ (at a given working distance) to efficiently capture each diffraction peak and sufficient adjacent baseline signal. The photo-sensor array 24 should also be sized for sufficient fiber-optic bundle cross-sectional width (perpendicular to the plane of the $2\theta$ angle) to provide adequate signal capture for subsequent signal processing in the CCD array and data processor.

In general, the fiber-optic bundle cross-sectional length is advantageously greater in the $2\theta$ direction than in the cross-sectional width normal to the $2\theta$ direction. Thus, for the two fiber-optic bundles 12 and 14, the output ends 16 and 18 are mated side by side prior to mating of the bundles to the fiber-optic face plate of the 2-D sensor array 24, using the mentioned potting fixture. The preferred method of mating the output ends is to mate the fiber-optic bundles long edge to long edge, to make the most effective use of typical rectangular CCD sizes.

Simple mating of the two fiber-optic bundles 12 and 14 is not adequate since light will scatter from one detector bundle, e.g., bundle 12, into the other detector bundle, i.e., bundle 14, (light can scatter as much as 2 to 3 optical fiber widths in such systems), thereby causing erroneous signals at improper positions. This is much more detrimental than light scattering between adjacent optical fibers within either individual bundle, which is one of the known parameters that limits resolution. To overcome the problem of light interfering between the two adjacent detector fiber-optic bundles, a partially to wholly light-tight (i.e., light non-transmissive) separating film 20 is sandwiched between the two fiber-optic bundles near the CCD interface. Such a light-tight separating film also serves to prevent undue stress on the fiber-optic bundles at the interface region of the fused and flexible region in proximity to ends 16 and 18 as schematically shown in FIG. 3. The fused region near each end 16 and 18 of the fiber-optic bundles has less cross-sectional area than the unfused region directly next to it. Accordingly, separating the fused ends with the flexible polymeric film 20 prevents undue pressure, and thereby minimizes premature breakage of fibers in the unfused section of each of the fiber-optic bundles near the fused region interface. The light-tight film 20 should be as thin as possible to prevent blocking out a large number of pixels in the 2-D photo-sensor array. While any suitable film material and film thickness may be employed for the light-tight film 20, a film thickness of 100 microns of a light-opaque material such as Transite film works well.

Photo-sensor array 24 is interconnected by way of a cable 4 to a data processor 2. The data processor 2 includes a CCD controller and a programmable computer for analyzing data representing stress in the sample.

Figure 4:
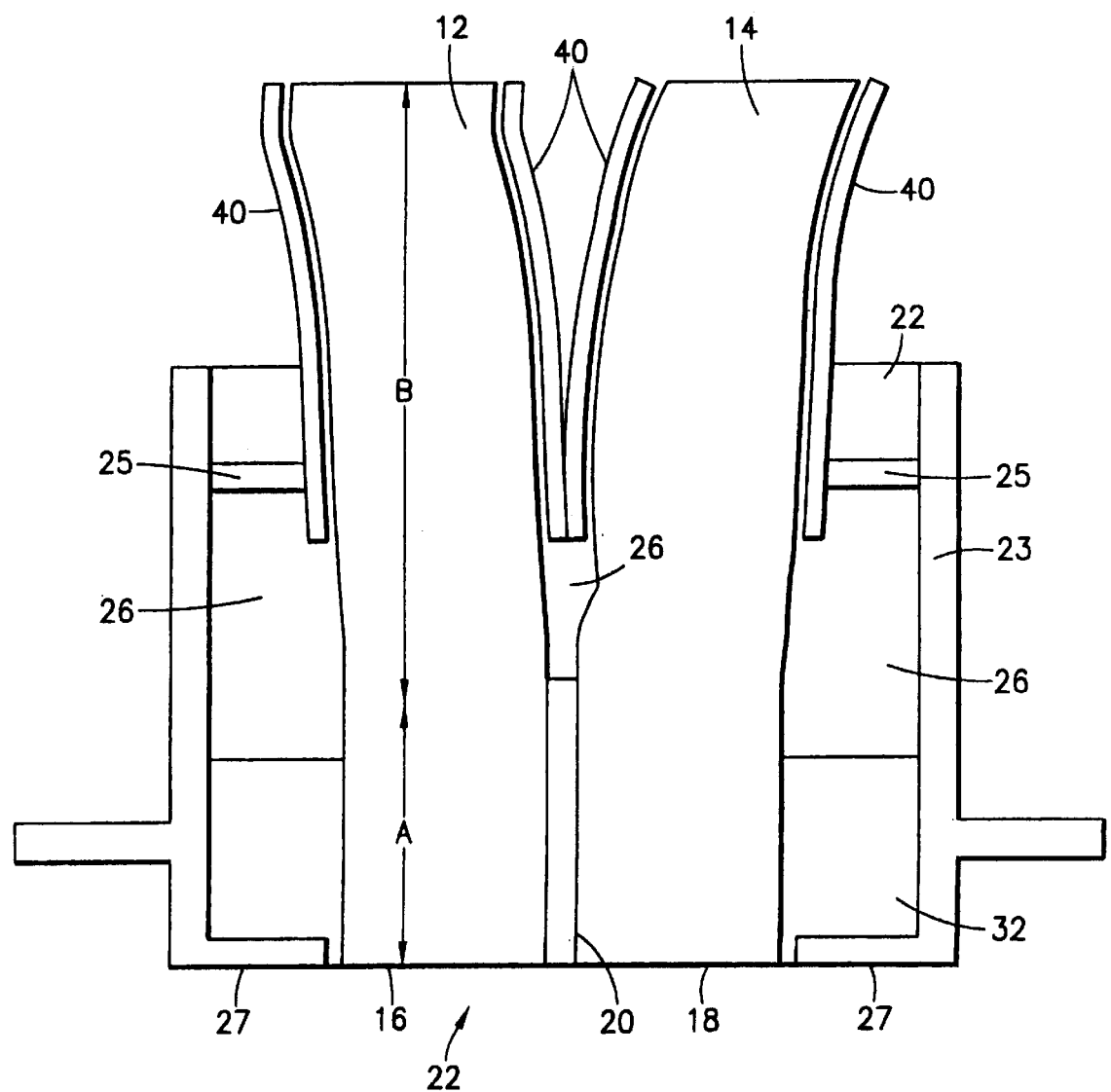
FIG. 4 is a schematic representation of a multiple zone rigid fixture used for fabricating a flexible and secure interface of fiber-optic bundles where they mate to the fiber-optic interface of the 2-D photo-sensor array.

FIG. 4 is a schematic representation of a three zone fixture enabling the mating of the bundles 12 and 14 in a close packed arrangement at the output ends 16 and 18. The unfused region B of each bundle includes respective loose optical fibers with a protective light blocking sheathing 40 which terminates before reaching the fused region A. The light-tight sheathing is typically a black butyl rubber material, with suitable thickness and durometer number (stiffness), that both mechanically protects the optical fibers, and prevents ambient light from entering the optical fibers. This type of sheathing is commonly used for flexible fiber-optic arrays. When working with isolated bundles, the sheathing 40 is normally terminated at some point along the fused region A at both the input and output ends of the bundle with a tight seal, leaving a short section of fused fiber-optic bundle exposed for mounting in a suitable fixture. However, with two bundles being mated side by side, the light-blocking protective sheathing 40 (which is much thicker than the separating film 20) must be terminated prior to the fused region in order for the bundles to be mated. FIG. 4 shows one preferred embodiment where the upper zone of fixture 23 enables termination of the light blocking sheathing prior to mating of the bundles. The sheathing 40 is terminated just beyond a back plate 25 of a mounting fixture 23, and is potted into place with a low temperature epoxy. Most commercially available low temperature epoxies are suitable. The sheathing is terminated and potted while still in flexible region B of the fiber-optic bundle. A middle zone of fixture 23 includes gap 26 that allows the flexible portions of the bundles 12 and 14 to come together just prior to the fused region A of each bundle. Though unsheathed in gap 26 the optical fibers are mechanically protected and light protected by surrounding fixture 23. In the lower zone of fixture 23 the fused region A of each of the two fiber-optic bundles 12 and 14 is potted in the rigid fixture 23 flush with the front face 27 of the fixture. The opening in the rigid fixture 23 is made slightly larger than the multiple fiber-optic bundles 12 and 14 to allow some potting material 32 to fill the gap, thereby preventing undue stress on the bundles. Once fully cured the entire face 27 of the rigid fixture 23 and the output ends 16 and 18 of the fiber-optic bundles 12 and 14 are polished flat to ensure optimal coupling to the fiber-optic faceplate of the CCD sensor array 24 of FIG. 3.

Figure 5:
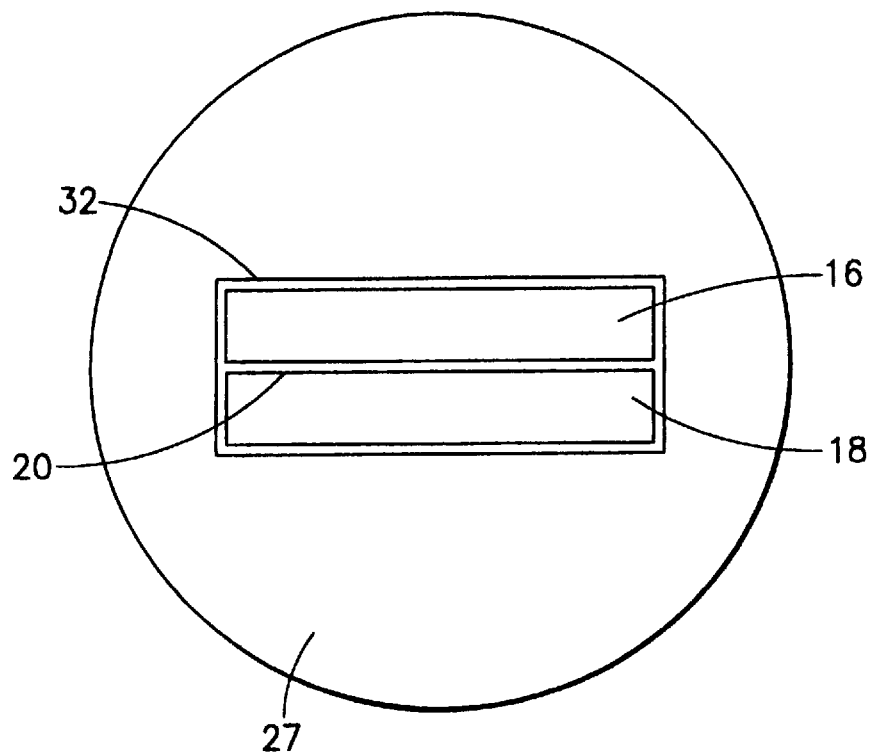
FIG. 5 represents an end view of two potted fiber-optic bundle ends forming a composite bundle end face that mates to the fiber-optic interface of the 2-D photo-sensor array.

FIG. 5 is a schematic representation of the end-on view of the potted end of a 2-D fiber-optic bundle subassembly whose output end mates the fiber bundles 16 and 18 sidewise, separated by a 0.1 mm thick partially light-tight film 20 and potted in an encapsulation medium 32 to present a flat end surface comprising the end surfaces of the fiber-optics bundles 16 and 18. In a preferred embodiment, the fixture 23 of FIG. 4 is machined into a circular shape that is not much larger than the cross-sectional size of the fiber-optic bundles. By polishing the fiber-optic bundle face 22 flush with the fixture face 27, the entire flat face can be pressed up against the flat fiber-optic face plate of the CCD sensor array 24 of FIG. 3 to ensure good optical coupling. The face 27 of the fixture 23 helps to ensure that the face 22 of the fiber-optic bundles rests flat on the face plate of the CCD sensor array 24. However, it is preferred to take steps to prevent excessive heat loss from the CCD sensor array (which is typically cooled to temperatures of $-30°$ to $-50°$ C. by thermo-electric cooler or other means to reduce read out noise and dark current) to the fixture 23. This can be accomplished by keeping the size of the fixture 23 sufficiently small, fabricating the fixture from low thermal conductivity material, and/or using geometrical methods such as recesses or holes in the face 27 to reduce thermal conduction pathways. Water cooling is the preferred method for removing the heat generated by the thermoelectric cooler. The 2-D photo-sensor array 24 preferably should be purged with dry gas during cooled operation to prevent moisture condensation on cooled electronic components.

A fiber-optic detector incorporating a two-dimensional (2-D) photo-sensor array 24 is a position sensitive detector but not like the linear or one-dimensional (1-D) photo-diode array (PDA). A 2-D photo-sensor array cannot be readily substituted for the PDA, as described in the art, because the 2-D CCD array will not provide the proper one dimensional output signal, as shown in FIG. 2 for stress analysis.

The predominant two-dimensional (2-D) photo-sensor array in commercial use today is the charge coupled device (CCD). Charge injection devices (CID) are relatively new, and thus limited in commercial usage at this time. Either CCD or CID devices or any other suitable 2-D photo-sensor array components may be employed in the broad practice of the present invention. Most commercially available 2-D photo-sensor arrays, e.g., CCDs, are not operative and provide no benefit in a fiber-optic position-sensitive detector for stress analysis, of the type described in U.S. Pat. Nos. 4,686,631; 5,148,458; 5,414,747, and 5,125,016.

The 2-D photo-sensor array 24 desirably employs the technique of Multi-Pin Phasing which can be optionally provided by the manufacturer of the photo-sensor array. The option of multi-pin phasing will significantly reduce the noise level of a given CCD compared to a PDA, or CCD without Multi-Pin Phasing, however, the charge storage capacity of the pixels comprising the CCD will be reduced by approximately one half. The option of Multi-Pin Phasing is not normally required if the CCD can be cooled to very low temperatures of minus $60°$ C. or lower, however, such temperatures are achieved using evacuated lense coupled CCDs. The method of direct fiber-optic coupling and purging with a dry gas creates a thermal short circuit preventing very low temperatures from being reached, thus the Multi-Pin Phasing option allows one to obtain a much lower dark current at higher temperatures. For example a Non Multi-Pin Phased CCD might exhibit a typical dark charge of 35 electrons per pixel-second at minus $40°$ C., while the same CCD with Multi-Pin Phasing might exhibit a typical dark charge of less than 0.1 electrons per pixel-second at minus $40°$ C. The lower charge storage capacity resulting from Multi-Pin Phasing is not detrimental for this invention, since the typical overall light levels created by the diffraction process are quite low.

The 2-D array preferably should be capable of incorporating a fiber-optic compatible image intensifier if so desired, however, an image intensifier will not necessarily be required in every circumstance, due to the much lower noise level possible with Multi-Pin Phased CCD.

This embodiment of the invention employs a cooled, scientific slow scan (low noise) readout, 2-D photo-sensor array 24 that provides significant, unexpected benefits to the stress analysis procedure. The 2-D photo-sensor array can be, for example, a rectangular front-illuminated scientific grade CCD, such as a 256×1024 pixel CCD array with 27 micron×27 micron square pixels, a 25 mm diameter variable gain, gated image intensifier, a Multi-Pin Phasing option, a fiber-optic window permanently mated to the image intensifier, thermoelectric cooling, water cooling, and dry gas purging ports. Such a CCD photo-sensor array 24 can be obtained from Princeton Instruments Inc. The 2-D photo-sensor array sends out a position-preserved intensity signal for each associated constituent pixel. The output will appear as a 2-D picture or image with intensity represented by gray-scale levels or color changes, depending on the colorimetric character of the output.

Figure 6:
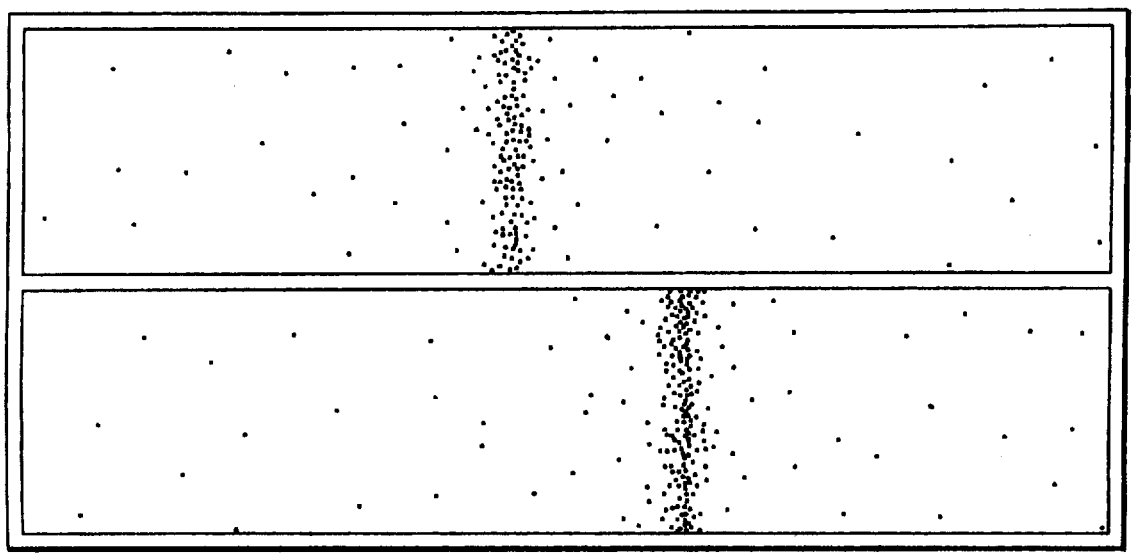
FIG. 6 represents a typical 2-D output image from two fiber-optic bundles monitoring an x-ray diffraction peak, each bundle monitoring a different side of the Debye ring, together with an outline of the fiber-optic bundles.

FIG. 6 shows a typical image output of the fiber-optic bundle/2-D photo-sensor array 24. Though diffraction peaks can be identified by the bright lines that pass through the image, there is no way of accurately determining their position from this unmodified image. This type of output is not useful or operative for stress analysis in accordance with the teachings of the aforementioned Ruud patents. These Ruud patents do not describe any method for converting a 2-D image to an appropriate signal suitable for stress analysis, nor does the art of 2-D photo-sensor technology enable the 2-D array to be operably employed in stress analysis in accordance with the teachings of the Ruud patents. A subsequent description teaches how to convert the 2-D image produced at the CCD into an equivalent one dimensional diffraction pattern as shown in FIG. 2. Mathematical curve fitting of the diffraction peaks of such one dimensional diffraction patterns can then be carried out for effective stress determination.

Only a very specific type of charge-coupled device (CCD) is operative in the stress analysis system described by U.S. Pat. No. 5,414,747. The majority of commercially available CCDs are ineffective in application to such stress analysis systems. In contrast to such teaching of U.S. Pat. No. 5,414,747 of use of charge-coupled devices, a CCD photo-sensor array in the x-ray detector is used differently than the linear photodiode array is used in the aforementioned patent. Specifically, a photodiode array (PDA) of the patent views only a one-dimensional signal which is directly output as the necessary diffraction peak spectrum for subsequent stress analysis. A CCD photo-sensor array, on the other hand, views a two-dimensional image which cannot be directly output in the necessary diffraction peak spectrum format.

Further, in U.S. Pat. Nos. 4,686,631, 5,148,458, and 5,414,747, the output ends of the two or more individual fiber-optic bundles are significantly separated when mated to separated individual PDAs. The arrangement of FIGS. 3 and 4 herein requires that two or more fiber-optic bundles be joined together in a tightly packed fashion to allow for mating to a single CCD photo-sensor- array. A specific binning procedure of the pixels of the CCD is then employed to create the necessary one dimensional diffraction peak spectrum format, as shown in FIG. 2. To make a 2-D image output work effectively for the Ruud stress analysis, the pixels in the 2-D array are binned (meaning that a number of individual pixels are combined into one large pixel, i.e., a super-pixel) in a very specific manner.

To obtain the desired one dimensional output of intensity versus diffraction angle for stress analysis, rather than a 2-D image output of the CCD, the system employs a software binning procedure, which converts the 2-D image input from the multiple fiber-optic bundles into separate one dimensional (1-D) diffraction spectra showing the diffraction peaks. The diffraction peaks can then be fit to a mathematical curve for precise diffraction angle determination, and subsequent stress determination.

Figure 7:
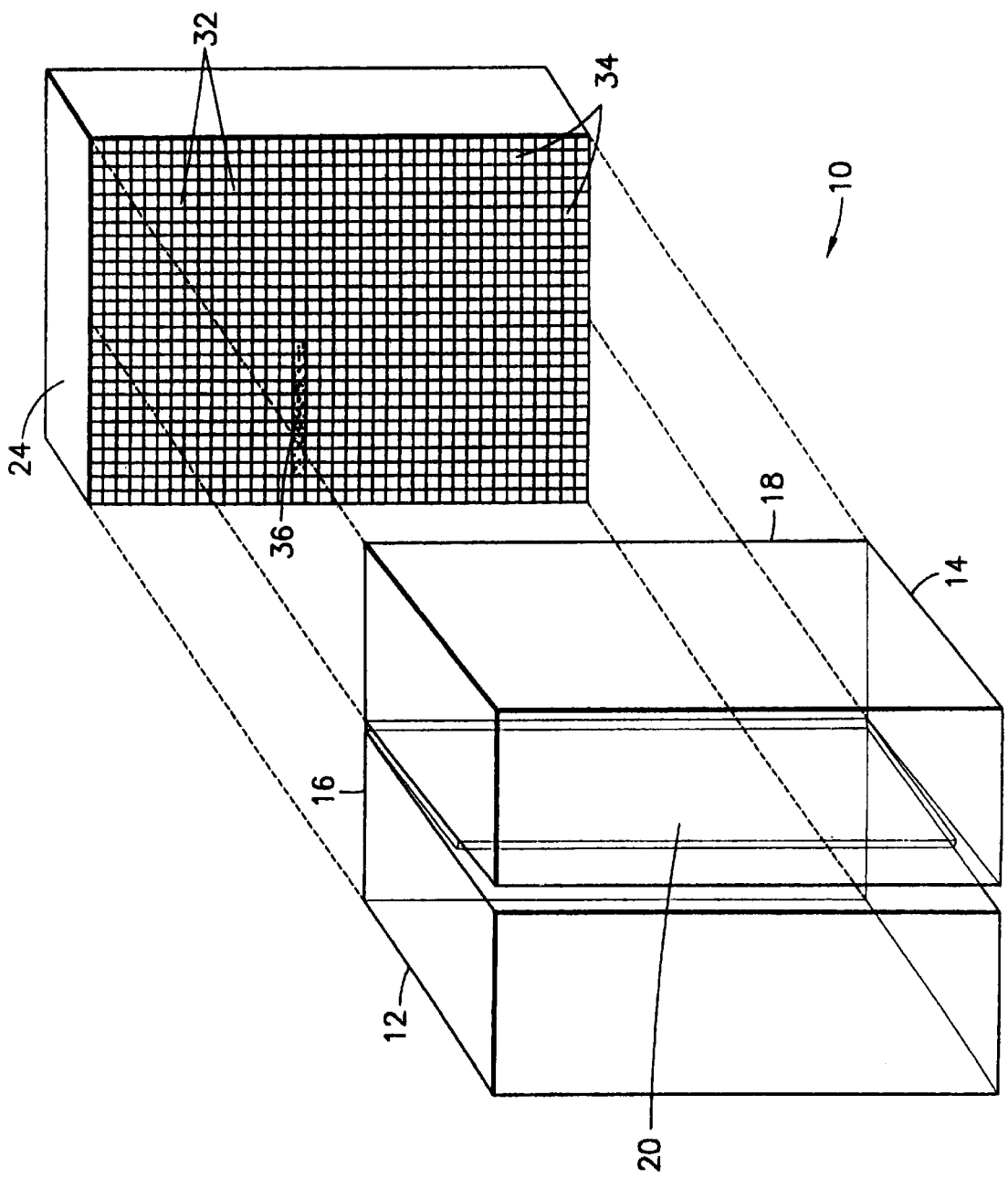
FIG. 7 is a schematic depiction of the orientation of fiber-optic bundles over pixels of the 2-D photo-sensor array.

FIG. 7 shows a schematic depiction of the two fiber-optic bundles 12 and 14 terminating in front of a single 2-D photo-sensor array 24 with pixels for carrying out the preferred binning procedure. As illustrated, the CCD/fiber-optic bundle subassembly 10 comprises the fiber-optic bundles 12 and 14 with the interposed light-tight membrane 20. The output faces 16 and 18 of bundles 12 and 14 directly mate to the fiber-optic face plate (not shown in FIG. 7) covering the CCD photo-sensor array 24. An intervening image intensifier can also be located between the fiber-optic face plate and the CCD array. For schematic purposes the geometrical positioning of the fiber-optic bundles is shown directly opposite the CCD array, since the output image position is preserved from the fiber-optic bundles 12 and 14 through the fiber-optic face plate and image intensifier to the CCD photo-sensor array 24. The perimeter of the composite output face (combined faces 16 and 18) is matched to the perimeter of an associated 2-D photo-sensor array, to yield the conjoint fiber-optic sensor assembly of the present invention.

The CCD output constitutes a two dimensional image of two aligned rectangles, one for each fiber-optic bundle, with each rectangle showing a bright line cutting across its width indicating where the peak is located. Advantageously, the arrangement of the CCD photo-sensor array provides significant improvement over other known x-ray detector systems.

A typical CCD has a large number of available pixels, but such pixels are all compacted onto a single two-dimensional grid. As disclosed previously, the fiber-optic bundles 12 and 14 are joined in the fixture 23 before they reach the CCD photo-sensor array 24 in order to efficiently utilize the active CCD area. This is not trivial, even for someone practiced in the art of fiber-optic arrays. The fiber-optic bundles 12 and 14 should be sized to fit within the CCD active area, but such bundles should also be sized appropriately for the working geometry of the x-ray diffraction apparatus. Thus, it is important to choose a proper CCD photo-sensor array size. Two or more fiber-optic bundles are then sized to mate to the CCD array. The fiber-optic bundles are sized and carefully brought together in the fixture, while still optically isolated, so that parts of the light image near the edge of one optical fiber-optic bundle do not interfere with parts of the light image near the edge of the adjacent fiber-optic bundle.

In FIG. 7 the CCD photo-sensor array 24 includes individual pixels 32 together with other pixels 34, aligned with the perimeter of the fiber-optic bundle head and shown in darker shading relative to the interior pixels 32. The peripheral pixels 34 are purposely not read, in order to maximize resolution and signal processing efficiency. Shown in a medial portion of the field of pixels to be read in fiber-optic bundle 12 is a group 36 of individual pixels (shown in darker shade than the other pixels to be read). The pixel group 36 is binned into a superpixel. Note that the number of individual pixels shown in FIG. 7 is for descriptive purposes only, and is far less than the actual number of pixels in a preferred embodiment of the invention. The long cross-sectional length of the two incoming fiber-optic bundles 12 and 14 (i.e., in the vertical direction in FIG. 7) coincides with the 2θ direction, and thus is the direction in which maximum resolution is generally desired. The short width of the two incoming fiber-optic bundles (i.e., the horizontal direction in FIG. 7) is normal to the 2θ direction. By binning the maximum number of pixels in the bundle width (normal to 2θ arc) direction, the detection area can be increased (helping to improve both the sensitivity and signal-to-noise ratio) without a loss of 2θ angular resolution.

In the vicinity of the fiber-optic bundle edges, a small number of pixel rows/columns 34 are rendered inoperative (they collect signal but are not read), as part of the overall binning procedure. This is done to allow for slight angle alignment errors that might occur between the fiber-optic bundles and the CCD, and to account for minor overall size discrepancies that may exist between the CCD and fiber-optic bundles. The number of pixels rendered inoperative is very small compared to the number that remain active. For example, in an embodiment utilizing a 256 by 1024 pixel CCD array with 27 micron by 27 micron square pixels, there are 128 pixels available across each fiber-optic bundle. If four pixel rows are rendered inoperative at each edge, then 120 pixels (128−4−4=120) can be binned into each super-pixel.

The fiber-optic bundle/2-D photo-sensor array assembly as described herein cannot be utilized in an x-ray diffraction system of the type disclosed by Ruud unless that system is appropriately modified in respect of the fiber-optic bundle/2-D photo-sensor array assembly and is operated with appropriately modified programming and software in the computer. The disclosure of U.S. Pat. No. 4,686,631 is incorporated herein by reference thereto.

The use of a single 2-D photo-sensor array offers numerous advantages over multiple PDAs. CCD arrays are available in a wide variety of sizes, and a suitably large size CCD can fit onto a single image intensifier maximizing the active detector area available for detection. Linear PDAs are limited in available sizes and cannot be tightly packed, such that only a limited total amount of active PDA area can be place on a single image intensifier. A single control system can be used to collect accumulated data from the CCD, while the multiple PDAs must be treated as separate data collection devices. Scientific CCD arrays can also have much lower noise levels than PDAs.

The computer performs a rapid pixel binning operation using custom software when CCD systems are employed as detectors for stress analysis. Neither hardware binning nor software binning tools provided by manufacturers of commercially available CCD units are satisfactory in application to such x-ray detector systems. A rapid binning procedure for large groupings of 100 or more pixels is required. It should be noted that binning of pixels is practiced in the use of scientific CCDs, however, such pixel binning operations are not effective for the current invention which requires large numbers of pixels (one preferred embodiment utilizes 120 pixels binned into a super-pixel) to be binned very quickly. The absence of any derivative nexus in the x-ray diffraction systems of the prior art, for such aspect of the present invention, is consistent with the fact that none of the software binning options for currently available commercial scientific CCDs are capable of binning in the manner of the present invention. In this respect, a key disadvantage of commonly practiced binning procedures is that they are either limited to small groups of pixels when hardware binned, or become prohibitively slow for large groupings of individual pixels. Tens of seconds, and even minutes, can be consumed for the binning of a single 2-D image utilizing prior binning techniques.

Hardware binning of pixels, with pixels being binned into shift registers during the read-out process, can be carried out very rapidly, however, the total allowable charge per super-pixel is limited to the charge capacity of the shift register pixels. For x-ray diffraction, fewer than 20 CCD pixels could typically be binned into each shift register pixel, before the shift register pixel becomes saturated. This is far too few for adequate x-ray diffraction operation of the present invention.

For this reason in the practice of the present invention, a rapid external software pixel binning procedure is used to bin the pixels to the desired format in less than 0.3 seconds. In this rapid binning procedure, the 2-D image obtained on the CCD array is exported from the CCD software as an unmodified 2-D data stream, a relative intensity being associated with each pixel, which then is processed by an algorithm in any suitable computer language, e.g., C++, to sum intensities of pixels in the desired format. Illustratively a data grid of 256 elements by 1024 elements by 2 bytes is used for storing the data from a CCD array having an array of 256×1024 pixels. The 2 bytes of range for each pixel accounts for the range of possible relative intensities associated with each pixel. The binning algorithm may be used in any desired x-ray diffraction system application.

Figure 8:
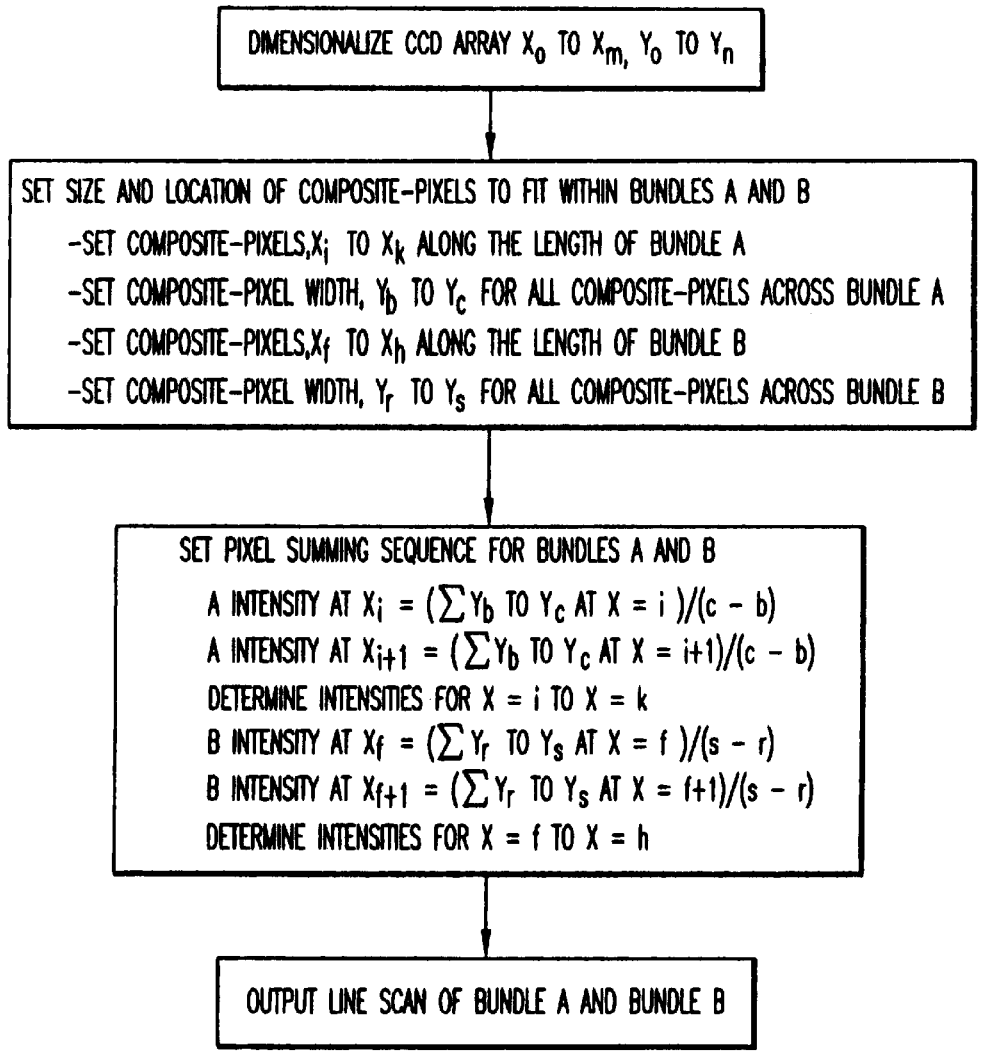
FIG. 8 is a flowchart and accompanying graph showing the methodology for pixel binning, according to one aspect of the invention.
Figure 8:
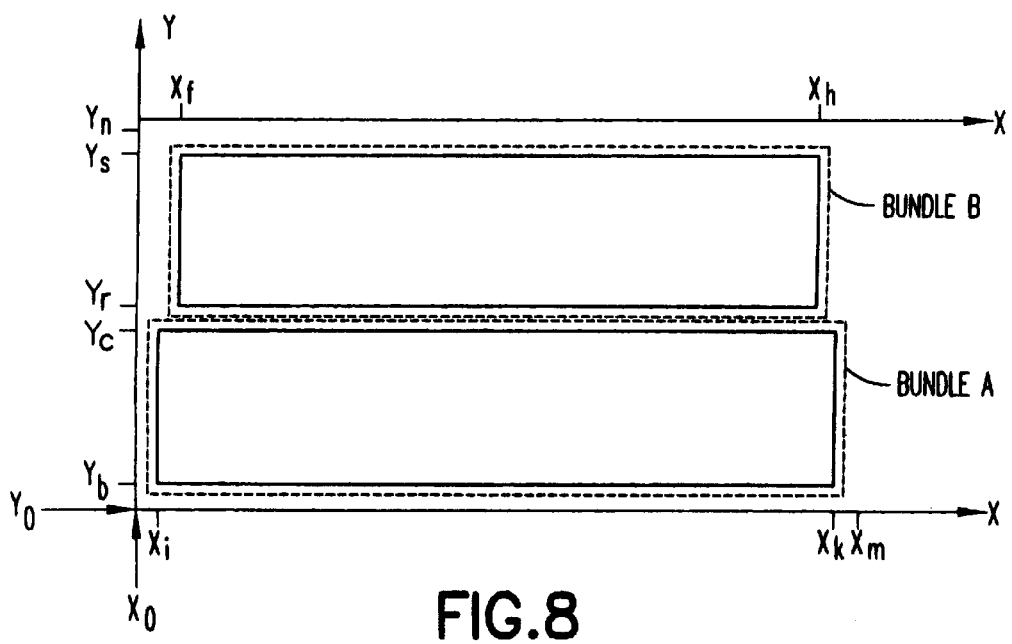

FIG. 8 is a schematic flow sheet of the methodology for pixel binning, according to one aspect of the invention. In this flow chart, progressing from top to bottom as illustrated, the CCD array is dimensionalized from $x_0$ to $x_m$ along the array in the 2θ direction and from $y_0$ to $y_n$ across the array normal to the plant of the 2θ direction. Next, the size and location of superpixels is set to fit within bundles A and B corresponding to fiber-optic bundle output faces 16 and 18 in the illustrative embodiment of FIG. 7. In such operation, the superpixels are set from $x_i$ to $x_k$ along the length of bundle A in the 2θ direction, and the superpixel width is set from $y_b$ to $y_h$ across each superpixel in bundle A. Correspondingly, the superpixels are set from $x_f$ to $x_h$ along the length of bundle B and the superpixel width is set from $y_r$ to $y_s$ across each superpixel in bundle B.

After the size and location of the superpixels is set, as described above, the pixel setting sequence is set for bundles A and B.

Intensity $x_i = (\Sigma y_b$ to $y_c$ at $x=i)/(c-b)$.

Intensity $x_{i+1} = (\Sigma y_b$ to $y_c$ at $x=i+1)/(c-b)$.

Intensities are determined for each superpixel x=i to x=k for bundle A.

For Intensities of the superpixels of bundle B, the algorithm is:

Intensity $x_f = (\Sigma y_r$ to $y_s$ at $x=f)/(s-r)$.

Intensity $x_{f+1} = (\Sigma y_r$ to $y_s$ at $x=f+1)/(s-r)$.

Intensities are determined for each superpixel x=f to x=h for bundle B.

The full image from the CCD array then is read into the data processor and processed to produce an output one dimensional diffraction spectrum of the type described in FIG. 2.

The illustrative embodiment of the invention has been described herein as encompassing the fiber-optic bundle/2-D photo-sensor array assembly including two discrete fiber-optic bundles. Preferably the bundles are of the same size (cross-sectional area) and shape to facilitate registration of the bundles into the geometrically regular head having the mated and side-wise abutting bundles, in an arrangement in which the bundles end at a common plane abutting the CCD array. Another embodiment may have more than two fiber-optic bundles and different sizes of fiber-optic bundles in relation to one another.

The invention has a number of unexpected benefits. Due to the much higher detector sensitivity and size selectivity, stress data can be acquired in a much shorter time interval with more flexible working geometries using 2-D photo-sensor arrays than using traditional PDAs. This makes the 2-D photo-sensor array based detector more useful in various respects:

1. The capacity to see low intensity peaks. Many materials and lower power x-ray sources produce extremely weak diffraction peaks (low peak-to-background ratio) at high back-reflected angles. These materials may have low crystallinity, or an obscuring surface condition, or high preferred orientation, or very little material may be available for diffraction at all (such as in the case of thin films). A much more sensitive 2-D photo-sensor array based detector (such as a CCD) has a much greater ability to observe such low intensity peaks that the PDA is not able to observe (or can only observe after very long data acquisition times). It also enables the use of lower power x-ray sources which can increase safety and portability.

2. The capability of providing faster measurements suitable for real-time analysis and greater sample throughput than PDA-based systems. A much faster data acquisition speed (as much as 1 to 2 orders of magnitude faster) is possible with 2-D photo-sensor arrays than with currently available PDA-arrays, when each is intensified and coupled to scintillation coated fiber-optic bundles. This is due to a much lower background noise of the CCD and greater active detector area of the CCD. High sensitivity enables the collection of quantifiable diffraction peaks used for stress determination in a shorter time interval. It allows the inventive detector the ability to collect real-time data on phenomena that change too rapidly for slower PDA detectors.

3. The ability to accommodate smaller x-ray beam spot sizes for enhanced focusing resolution, and spatial resolution of material being measuring. Improved focusing resolution of a position sensitive detector can be obtained with a smaller irradiated spot size on the sample surface. Another benefit of smaller spot size is improved resolution when mapping stress across the surface of a material. This is highly advantageous in material regions where the stress changes drastically over a small distance, such as over a weld joint. Reducing the irradiated spot size significantly reduces the diffracted x-ray intensity reaching the detector, and in the prior art requires much longer data acquisition times, or some cases rendering the prior art unusable. The increased sensitivity afforded by the invention allows one to use smaller spot sizes at much faster data collection times than prior art.

4. The provision of longer working distances. In some instances one cannot obtain close access to a part for stress measurement. This is especially true if one wants to measure stress in-situ during a process step such as thermal treatment. With the limited number of pixels available to a system employing PDAs mated to a single image intensifier, increasing the working distance (distance from the detector to the sample surface) will result in a significant loss of angular range. Eventually the background baseline on either side of the diffraction peak is lost, rendering the data useless. Adding additional PDAs and a second image intensifier is a potential solution, but only at great expense and with significant increase in complexity. The larger detection area of a CCD allows one to increase the working distance while still maintaining a sufficiently large angular range. The greater detector sensitivity also helps to compensate for the lower x-ray intensity that occurs over greater working distances due to air attenuation.

5. The use of more extensive information from the Debye ring. Although the aforementioned Ruud patents make use of a 1-D diffraction spectrum for determining stress, other information can be garnered from a 2-D image prior to binning it into a line scan for stress analysis. The 2-D image components of the present invention actually observe a small portion of the Debye ring. By this improvement of the present invention, the continuity of the Debye ring (solid line versus a spotty output) can be related to the grain size of the material.

6. The optional elimination of the image intensifier component of the system. An image intensifier magnifies the light signal prior to reaching the photo-sensor array, but current commercial image intensifiers limit the linear resolution of the detector to approximately 75 microns. When detector sensitivity is of most concern an image intensifier is most effective, however when angular resolution is as critical as sensitivity the image intensifier could be optionally eliminated from the apparatus, and the subsequent detector resolution will be much closer to that of the photo-sensor array pixel width (typically 9 to 25 microns in size). PDAs have been shown to be inadequate for stress analysis of the type taught in the aforementioned Ruud patents without the use of an image intensifier, due to high internal noise levels. On the other hand, the very low noise levels of the 2-D photo-sensor array enables their use for x-ray diffraction without such an image intensifier. For example, in those materials which exhibit very little diffraction peak shift as a function of stress, such as many ceramics, the angular resolution of the detector must be very high.

7. Better matching of detector properties to low intensity diffraction stress analysis. PDAs exhibit relatively large amounts of noise, but can handle a very large x-ray dose. Thus they are better suited for applications where large amounts of measurable light are present, and where the peak intensity is significantly greater than the background intensity (large peak-to-background ratio). High sensitivity scientific CCDs are far more light sensitive than PDAs. Intensified CCDs are capable of single photon counting. Thus they are best suited for detection weak diffraction spectra typically encountered in x-ray stress analysis.

Against such background, the present invention relates in one aspect to an x-ray diffraction system for x-ray diffraction analysis of a sample, such system comprising: at least two fiber-optic bundles, each bundle sheathed in a suitable light blocking material, each bundle terminating at input and output ends, with the output ends being in registration with one another so that the output ends of the fiber-optic bundles lie in a plane to form a output end face including output ends of such fiber-optic bundles; a light transmission-restrictive layer disposed between adjacent different fiber-optic bundles at output end portions thereof to restrict light transmission between the bundles at the output end portions thereof; and a two-dimensional photo-sensor array in light-receiving relationship to the output end face of fiber-optic bundles, with the input ends of the fiber-optic bundles being non-contiguous and arrangeable for positioning in relation to a sample receiving incident x-radiation thereon, with a thin scintillation coating adhered to the face of the input ends of the bundles for converting the incident x-ray spectrum to an equivalent light spectrum which enters the bundles so that the diffracted x-radiation impinging on the input ends of the fiber-optic bundles is transmitted therein as visible light through the output end face to the two-dimensional photo-sensor array; and signal processing means operatively coupled to the two-dimensional photo-sensor array for acquisition and processing of data from the two-dimensional photo-sensor array for the x-ray diffraction analysis of the sample.

The signal processing means in the above-described x-ray diffraction system may suitably comprise a data processor consisting of an electronic controller for the photo-sensor array and a programmable computer programmed to produce from acquired data x-ray diffraction information about the sample, e.g., stress analysis information. The programmable computer may be programmed to conduct a binning algorithm for summing the contents of pixels of the two-dimensional photo-sensor array into a superpixel format to provide the x-ray diffraction information desired. The pixel summation may be conducted in a direction of the fiber-optic bundle input end which is normal to the 2θ direction in order to create the desired 1-D diffraction spectrum necessary for stress analysis.

Yet another aspect of the invention relates to a method of collecting diffraction x-radiation diffracted from a sample receiving incident x-radiation thereon, such method providing at least two elongate fiber-optic bundles in receiving relationship to diffracted x-radiation from the sample; converting the position sensitive x-ray spectrum to an equivalent position sensitive visible light spectrum by use of a thin scintillation coating adhered to the x-ray receiving face, or input face of the fiber-optic bundles; conveying the equivalent position sensitive light spectrum through each of the fiber-optic bundles to an output end opposite the input end receiving the x-radiation diffracted from the sample; providing a two-dimensional photo-sensor array in light spectrum receiving relationship to such ends of the fiber-optic bundles opposite the input ends receiving x-radiation diffracted from the sample; and processing data from the two-dimensional photo-sensor array receiving the equivalent position sensitive light spectrum, to yield a one-dimensional diffraction spectrum output.

Instead of a 2-D CCD photo-sensor array 24 as shown in FIG. 3, the array may use a CID, or other photo-sensor array which is capable of providing a two dimensional image in response to impingement of diffracted x-radiation thereon. The charge couple device 24 or other photo-sensor array is schematically illustrated as being joined by a signal transmission cable 4 to data processor 2 including a CCD controller and a programmable computer for providing an output x-ray diffraction peak spectrum for the sample being analyzed.

Thus, while the invention has been described illustratively herein with reference to various specific embodiments, aspects and features, it will be recognized that the invention is not thus limited, but encompasses numerous variations, modifications and other embodiments, and accordingly such other variations, modifications and other embodiments are to be regarded as being within the spirit and scope of the invention as claimed.

What is claimed is:

1. A method for determining stress in a crystalline sample, the method comprising the steps of:
   a. diffracting an x-ray beam from a surface of the crystalline sample to multiple channels of an x-ray detector, the diffracted x-rays forming an x-ray image;
   b. detecting and converting the x-ray image to an intensity proportional visible light image;
   c. conveying the visible light image through a multi channel image preserving media to a two-dimensional CCD array, each part of the image being incident upon a different region of the two-dimensional CCD;
   d. storing relative magnitudes of intensities of the visible light image in pixels of the two-dimensional CCD array as quantities of electrical charge;
   e. converting the quantities of charge to a digitized representation of the visible light image and storing the digitized representation in a randomly accessible memory;
   f. binning pixels of the digitized representation into superpixels in a one dimensional digitized representation in the randomly accessible memory, the one-dimensional digitized representation including an identifiable angular location of an x-ray diffraction peak intensity; and
   g. determining stress in the crystalline sample by analyzing any shift of angular location of the x-ray diffraction peak intensity.

2. The method of claim 1 wherein:
   h. the binning of pixels is accomplished by accumulating the magnitudes of the digital representations in sequence by first and second arrays of pixels;
   i. first, the magnitudes of a first row of the first array of pixels are accumulated and stored as a magnitude of a first superpixel of the first array of pixels;
   j. second, the magnitudes of another row of the first array of pixels are accumulated and stored as a magnitude of a second superpixel of the first array of pixels;
   k. repeat step j. until magnitudes of superpixels are accumulated for each row of the first array of pixels;
   l. then the magnitudes of a first row of the second array of pixels are accumulated and stored as a magnitude of a first superpixel of the second array of pixels;
   m. thereafter, the magnitudes of another row of the second array of pixels are accumulated and stored as a second superpixel of the second array of pixels; and
   n. repeat step m. until the magnitudes of superpixels are accumulated for each row of the second array of pixels.

3. The method of claim 1 wherein said crystalline sample includes an integrated circuit material.

4. The method of claim 1 wherein the two-dimensional CCD array comprises a multi-pin phasing CCD array.

5. The method of claim 1 wherein said crystalline sample comprises a semiconductor material.

6. The method of claim 1 wherein said crystalline sample comprises a conductor.

7. The method of claim 1 wherein in said step of binning pixels, a region of peripheral pixels of the digitized representation is not read, thereby enhancing resolution and signal processing efficiency.

8. The method of claim 1 wherein the step of binning pixels of the digitized representation into superpixels comprises binning groupings of at least 100 pixels.

9. A method for determining a property of a material sample, wherein said property is selected from the group consisting of stress, composition, texture and dimensional characteristics, such method comprising the steps of:
   a. diffracting an x-ray beam from a surface of the material sample to multiple channels of an x-ray detector, the diffracted x-rays forming an x-ray image;
   b. detecting and converting the x-ray image to an intensity proportional visible light image;
   c. conveying the visible light image through a multi channel image preserving media to a two-dimensional photosensor array, each part of the image being incident upon a different region of the two-dimensional photo-sensor array;
   d. storing relative magnitudes of intensities of the visible light image in pixels of the two-dimensional photosensor array as quantities of electrical charge;
   e. converting the quantities of charge to a digitized representation of the visible light image and storing the digitized representation in a randomly accessible memory;
   f. binning pixels of the digitized representation into superpixels in a one dimensional digitized representation in the randomly accessible memory, the one-dimensional digitized representation including an identifiable angular location of an x-ray diffraction peak intensity; and g. determining said property in the material sample by analyzing any shift of angular location of the x-ray diffraction peak intensity.

10. The method of claim 9 wherein:

h. the binning of pixels is accomplished by accumulating the magnitudes of the digital representations in sequence by first and second arrays of pixels;

i. first, the magnitudes of a first row of the first array of pixels are accumulated and stored as a magnitude of a first superpixel of the first array of pixels;

j. second, the magnitudes of another row of the first array of pixels are accumulated and stored as a magnitude of a second superpixel of the first array of pixels;

k. step j. is repeated until magnitudes of superpixels are accumulated for each row of the first array of pixels;

l. then the magnitudes of a first row of the second array of pixels are accumulated and stored as a magnitude of a first superpixel of the second array of pixels;

m. thereafter, the magnitudes of another row of the second array of pixels are accumulated and stored as a second superpixel of the second array of pixels; and n. step m. is repeated until the magnitudes of superpixels are accumulated for each row of the second array of pixels.

11. The method of claim 9 wherein said material sample includes an integrated circuit material.

12. The method of claim 9 wherein the two-dimensional photosensor array comprises a CCD array.

13. The method of claim 12 wherein the CCD array comprises a multi-pin phasing CCD array.

14. The method of claim 9 wherein said material sample comprises a material selected from the group consisting of conductor materials and semiconductor materials.

15. The method of claim 9 wherein in the step of binning pixels, a peripheral region of pixels of the digitized representation are not read, thereby enhancing resolution and signal processing efficiency.

16. The method of claim 9 wherein the step of binning pixels of the digitized representation into superpixels comprises binning groupings of at least 100 pixels.

17. The method of claim 9 wherein said property comprises stress.

18. The method of claim 9 wherein said property comprises composition.

19. The method of claim 9 wherein said property comprises texture.

20. The method of claim 9 wherein said property comprises a dimensional characteristic.

* * * * *